United States Patent [19]

Rosenberg

[11] Patent Number: 5,374,269
[45] Date of Patent: Dec. 20, 1994

[54] METHOD AND INSTRUMENTS FOR ACL RECONSTRUCTION

[75] Inventor: Thomas D. Rosenberg, Salt Lake City, Utah

[73] Assignee: American Cyanamid Company, Wayne, N.J.

[21] Appl. No.: 931,171

[22] Filed: Aug. 17, 1992

Related U.S. Application Data

[62] Division of Ser. No. 472,724, Jan. 31, 1990, Pat. No. 5,139,520.

[51] Int. Cl.$^5$ .......................... A61B 17/00; A61F 5/00
[52] U.S. Cl. ......................................... 606/80; 606/86; 606/88
[58] Field of Search .......... 606/80, 79, 86, 87, 606/88, 96, 97, 98; 408/203.5, 204, 224, 227, 229

[56] References Cited

U.S. PATENT DOCUMENTS

| | | | |
|---|---|---|---|
| D. 331,464 | 12/1992 | Rosenberg et al. | D24/147 |
| 2,243,718 | 5/1941 | Moreira | 606/80 |
| 3,867,932 | 2/1975 | Huene | 606/80 |
| 3,892,232 | 7/1975 | Neufeld | 128/92 |
| 4,312,337 | 1/1982 | Donohue | 128/92 |
| 4,341,206 | 7/1982 | Perrett et al. | 128/92 |
| 4,450,834 | 5/1984 | Fischer | 606/80 |
| 4,509,516 | 4/1985 | Richmond | 128/303 |
| 4,590,929 | 5/1986 | Klein | 128/92 |
| 4,751,922 | 6/1988 | DiPietropolo | 606/80 |
| 4,823,780 | 4/1989 | Odensten et al. | 128/92 |
| 4,830,000 | 5/1989 | Shutt | 606/80 |
| 4,950,270 | 8/1990 | Bowman et al. | 606/72 |
| 4,985,032 | 1/1991 | Goble | 606/96 |
| 5,047,034 | 9/1991 | Johnson | 606/87 |
| 5,190,548 | 3/1993 | Davis | 606/80 |
| 5,192,293 | 3/1993 | Cartwright | 606/80 |

OTHER PUBLICATIONS

*Techniques in Orthopaedics*, Vol. 5, Arthroscopic Surgery Update, John B. McGinty, M. D., Aspen Systems Corporation (1985).

*Orthopedic Catalog*, Richards Manufacturing Co., Inc. (1981).

Zimmer Catalog, Medical/Surgical Products, p. 170 (1980).

*Primary Examiner*—Michael A. Brown
*Attorney, Agent, or Firm*—D. E. Denninger

[57] ABSTRACT

A drill bit having a small-diameter shank, an abbreviated drilling head, and a smooth transition portion between the shank and the head. The drill bit is particularly useful for drilling femoral tunnels during reconstruction of cruciate ligaments.

10 Claims, 7 Drawing Sheets

METHOD AND INSTRUMENTS FOR ACL RECONSTRUCTION

This application is a division of 07/472,724, file Jan. 31, 1990, now U.S. Pat. No. 5,139,520.

TECHNICAL FIELD

The present invention relates to an improved method for reconstruction of a torn anterior cruciate ligament ("ACL") using endoscopic techniques, as well as new and improved instruments for use with the method.

BACKGROUND ART

Damaged ligaments, cartilage and tendons in joints are not an uncommon occurrence, particularly with today's emphasis on physical activity and conditioning. One of the joints which requires particular skill and presents particular difficulties in repairing is the knee joint.

Numerous improvements in repairing damage to knee joints have been made over the years, and some of the major advances involve endoscopic techniques and arthroscopic procedures. Arthroscopic surgery is particularly useful in excising or repairing damaged knee cartilage.

Endoscopic techniques have also been developed for use in repair and reconstruction of damaged anterior cruciate ligaments (ACL) and posterior cruciate ligaments (PCL). When the ACL in particular has ruptured and is nonrepairable, it is usually replaced in young adults and the knee reconstructed through use of grafts (biological or synthetic). Some known methods and techniques which have been used to repair and replace ACL ruptures with grafts are discussed, for example, in Moore U.S. Pat. No. 4,773,417, Goble U.S. Pat. No. 4,772,286 and an article by Goble entitled "FLUOROARTHROSCOPIC ALLOGRAFT ANTERIOR CRUCIATE RECONSTRUCTION", Techniques Orthop. 1988 2(4): 65–73.

The function of the real cruciate ligaments is complicated. The ACL and PCL are three-dimensional structures with broad attachments and a continuum of fibers. These fibers are of different lengths, have different attachment sites, and are under different tensions. Although many current substitutes for cruciate ligaments have not duplicated the complex orientation and operation of normal ACLs, they operate the best and mimic the normal ACL operation the best when they are placed isometrically. "Isometrically" positioned means that the length of the substitute ligament will not change during annular movement of the tibia relative to the femur; the distance between the affixed ends of the ligament remains a constant. Isometric placement maximizes the number of fibers that can be taut throughout the range of motion of the knee and allows for early knee motion without generating high ligament strains.

Correct isometric positioning of the ACL graft thus is an important factor for a successful operation. Correct isometric placement reproduces corresponding femoral and tibial anatomic attachment sites and will allow an ACL graft to mimic the normal ACL. Isometrically placed grafts provide the most stable knees. Non-isometric graft placement can result in plastic deformation of the ACL substitute, postoperative laxity, abnormal kinematics, or failure of fixation.

The importance of accurate placement of an ACL substitute is shown by the fact that graft placements sometimes only several millimeters apart produce significantly different strains in the cruciate substitute. A placement of the ACL origin or insertion which is too anteriorly placed in the knee joint results in a ligament that is taut in flexion, but lax in extension. Posterior placement causes the ligament to be taut in extension, but lax in flexion. Only isometric placement provides stability throughout the range of motion.

It is an object of the present invention to provide an improved method using endoscopic techniques for reconstruction of ACLs. It is a further object to provide isometric placements of ACL substitutes, and isometric placements which are objectively accurate and reproducible.

It is still a further object of the invention to provide an ACL replacement which is minimally invasive in order to minimize trauma and facilitate faster patient healing and rehabilitation. It is another object to provide a method of ACL reconstruction which preferably uses biological grafts from the patient and which provides similar and beneficial results whether patellar tendon grafts, semitendinosus tendon grafts, or other ACL substitutes are used.

It is still another object of the present invention to provide a new and improved method for assuring isometric placement of the ACL graft, and for minimizing the chance of PCL damage.

Further objects of the invention include development and use of improved instruments for ACL operations which help assure proper isometric graft placement, help prevent damage to the PCL, and provide an improved method for ACL reconstruction.

DISCLOSURE OF INVENTION

The above and other objects of the invention are met by the inventive method of ACL reconstruction and instrumentation which are disclosed and claimed in this application.

For the improved method, the knee joint is inspected arthroscopically to confirm the rupture and possibly take care of other defects. The patellar tendon or semitendinosus tendon is harvested from the patient for use as the graft, or another ACL substitute is obtained. The graft is prepared for later implantation. Semitendinosus tendon grafts are preferably divided into sections and the sections are formed together into a bundle. Elongated sutures are stitched at the ends of the graft bundles for use in implanting the graft and affixing it in place. For patellar tendon grafts, the bone plugs (or "blocks") at each end are shaped and sized for later use.

The torn ACL stumps are studied and partially removed if necessary. Notchplasty is preferably performed to expand the intercondylar notch. Both manual and powered instruments can be used for this procedure.

The tibial attachment site for the ACL graft is determined. A tibial drill guide mechanism guides a K-wire from a point 20–25 mm below the knee joint to the former ACL attachment site. A point on the guide mechanism is placed on the former site and a drill sleeve ("or bullet") is forced into the bone at the requisite position for drilling the tibial tunnel. A cannulated drill bit is overdrilled on the K-wire forming the tunnel.

The site for drilling the tunnel in the femur is determined isometrically. A proposed site is selected and tested for isometry. A pilot hole of a pre-specified size and depth is formed at that site. The pilot hole can be formed with a K-wire drill bit having graduated markings thereon, or preferably a K-wire having a reduced-size diameter tip and shoulder thereon. A threaded peg with an elongated suture attached is then screwed and anchored in place in the pilot hole at the proposed site. A hand held cannulated driver with an elongated sleeve and suture retention member are utilized. The threaded peg and sleeve end have mating cross-sectional sizes and shapes so the peg can be screwed in with the driver.

Once the suture anchor is installed, the sutures are passed through a centering plug and through the isometer and affixed tightly in place on the back of the isometer. The isometer is unlocked and readings are taken during movement of the knee.

If the proposed site is isometric, then a K-wire is inserted as a guide pin and a closed-end tunnel is drilled into the femur at that site. If the proposed site is not isometric, then the test is repeated at another site until isometry is reached. The femoral tunnel is drilled using a drill bit with an abbreviated drill head, a reduced sized shank, and a smooth transition area between the head and shank. This drill prevents damage to the posterior cruciate ligament and permits ease of removal from the drilling site.

The edges of the tibial and femoral tunnels are chamfered with a rasp to prevent abrasion and possible damage to the new graft.

The graft is implanted with one end secured in the closed-end femoral tunnel and the other end secured to the tibia adjacent to the tibial tunnel. With a patellar tendon graft, the bone plug on the leading end is locked in place in the femoral tunnel preferably with a unique interference screw. The bone block on the trailing end is secured by bone staples or the like in a trough or channel formed in the tibia below the tunnel entrance. Alternately, elongated sutures can be stitched onto the bone block on the leading end of the graft and then passed through a suture passing channel formed in the femur. The sutures are secured to a button on the lateral face of the femur.

With a semitendinosus tendon graft, the bundles with elongated sutures are passed or pulled through the osseous tunnels. A suture passing channel is preferably formed from the closed-end femoral tunnel to the lateral face of the femur and the sutures are passed through it with a pull-through wire. Once the leading end of the graft is positioned in the socket, the sutures are tightly affixed to a button. The sutures at the trailing end of the graft are affixed to a screw or post positioned on the tibia adjacent the entrance to the tibial tunnel. The post has a washer under its head to assure a tight connection between the post and sutures.

BEST MODE FOR CARRYING OUT THE INVENTION

For a knee reconstruction involving a torn anterior cruciate ligament (ACL), the procedure begins with a general anesthesia being administered to the patient. The patient is positioned supine on the operating table. The affected limb is secured in a thigh holder after a tourniquet is put in place. The surgical site is prepped and draped with a sterile seal.

Often a suitable autograph is harvested and the anterior tibea cortex exposed before the prepared knee is examined by arthroscopic procedures. Standard anterolateral and anteromedial portals are made for the diagnostic arthroscopy. The fat pad is pushed away from the area by distension of the knee. Any observed meniscal damage, osteophyte and unstable joint surfaces are appropriately treated by standard arthroscopic techniques and the status of the cruciate ligaments is confirmed.

Figures 1, 2, 3, 4:
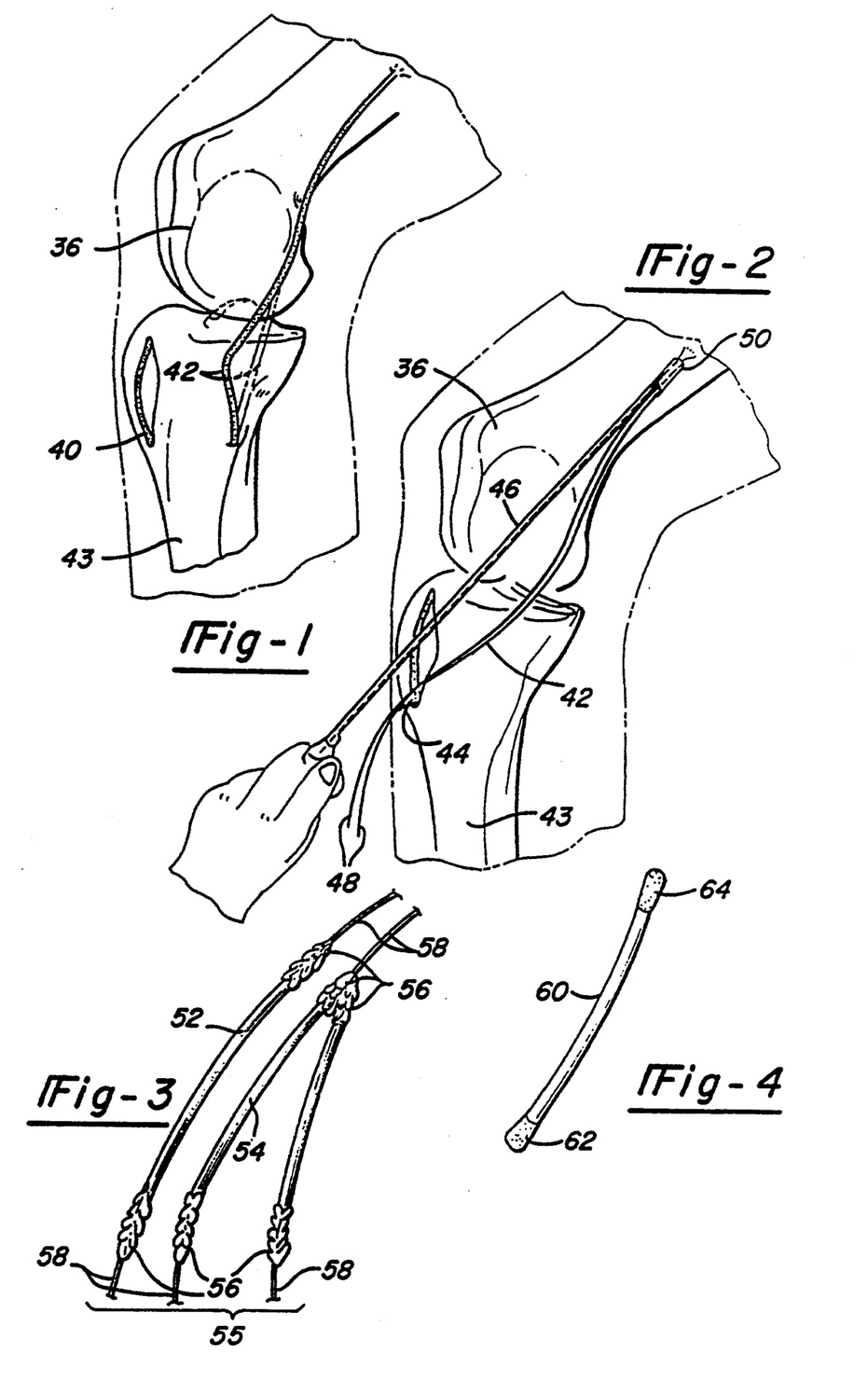
FIGS. 1 and 2 are schematic perspective views of the harvesting of the semitendinosus tendon for use as an ACL replacement in accordance with the present invention.
FIG. 3 illustrates a representative semitendinosus tendon prepared for use as an ACL graft in accordance with the present invention.
FIG. 4 illustrates a patellar tendon harvested and ready for use as an ACL graft in accordance with an alternate embodiment of the present invention.

The graft harvesting step use the procedure depends on the type of ACL substitute that is to be utilized. If a semitendinosus graft of the patient is to be utilized, an incision 40 is made over the pes anserinus in line with the fibers of the sartorius (FIG. 1). The sartorius is split (opened) to reveal the semitendinosus and gracilis tendons. The semitendinosus tendon 42 is isolated from the muscle and detached from the tibia 43. Tension is placed on the tendon by the index finger of one hand while it is being isolated and detached. The detached end of the tendon is prepared for grasping by installation of sutures using a No. 2 Ticron suture and a tendon needle. Preferably, a series of six whip stitches 44 are placed along each side of the loose end of the tendon (FIG. 2). The multilevel clasping sutures provide an excellent grasping fixation of the suture tendon junction.

The semitendinosus tendon is removed by a tendon stripper 46, preferably a closed-end tendon stripper made by Acufex Microsurgical, Inc., Norwood, Mass. (Part No. 013550). After the ends of the suture and loose end of the tendon are threaded through the tendon stripper, the tendon is grasped and held in tension manually at the ends 48 of the sutures 44. The stripper is slowly advanced up the length of the tendon until it is completely separated from the femur 36 and delivered. The stripper circumferentially divides the tendon using its sharp round leading edge 50. With this procedure, the length of the tendon is maximized.

The semitendinosus tendon is then prepared for later use as the ACL substitute. It is measured and divided into several segments or sections (FIG. 3). Usually individual segments 52 and sometimes doubled over segments 54 are utilized. No. 2 Ticron sutures 56 are attached to the ends of the graft sections for use in pulling the composite graft through the osseous tunnel and securing it at each end (as later explained). The loose ends 58 of the sutures provide satisfactory grasping fixation of the individual sections of the composite graft 55. The graft segments 52 and 54 are preferably approximately 6-8 cm in length and as a group or bundle 55 are about 8-11 mm in diameter.

If a patellar tendon graft 60 (FIG. 4) is to be utilized, then it is removed from the tibia and kneecap. An incision is made medial to the infrapatellar tendon and the patellar tendon is harvested using conventional techniques. Small blocks ("plugs") of bones 62 and 64 are taken and retained at each end of the tendon to aid in later securing the graft in the knee. The blocks of bone 62, 64 are sized using 1 mm incremental sizing tubes to obtain close conformity between the graft size and the tunnel size. This is necessary for optimal healing to occur. Once size is determined, the corresponding drill bit or bits are selected for later use in forming the tunnel in the tibea and the socket in the femur.

Although the present inventive method is preferably used with a semitendinosus tendon graft or patellar tendon graft, it is understood that the invention can be used to assure isometric placement of ACL replacements and a beneficial and advantageous ACL reconstruction utilizing any of the known grafts and ACL substitutes. Known ACL substitutes include autogenous tendons, frozen and lyophilized tendon allografts, and a variety of synthetic materials.

If, for example, another type of ACL graft is to be utilized instead of the semitendinosus or patellar tendons, it should be prepared in a similar manner. No. 2 Ticron sutures are attached at the ends of the graft in some conventional manner to aid in grasping, manipulating and securing the graft in place. Incremental sizing tubes are used to size the graft and select the appropriate drills for forming the tunnel. Installation and attachment of the graft to the femur and tibia are the same as that which will be described below relative to placement and attachment of a semitendinosus tendon.

After confirming a rupture of the ACL and taking steps to prepare the appropriate graft, a portion of the synovium and ligament stump is excised with conventional instrumentation to facilitate visibility during implantation of the graft. Care should be taken at this point to protect the PCL and avoid injury to it and its synovium.

Figures 5, 6, 7:
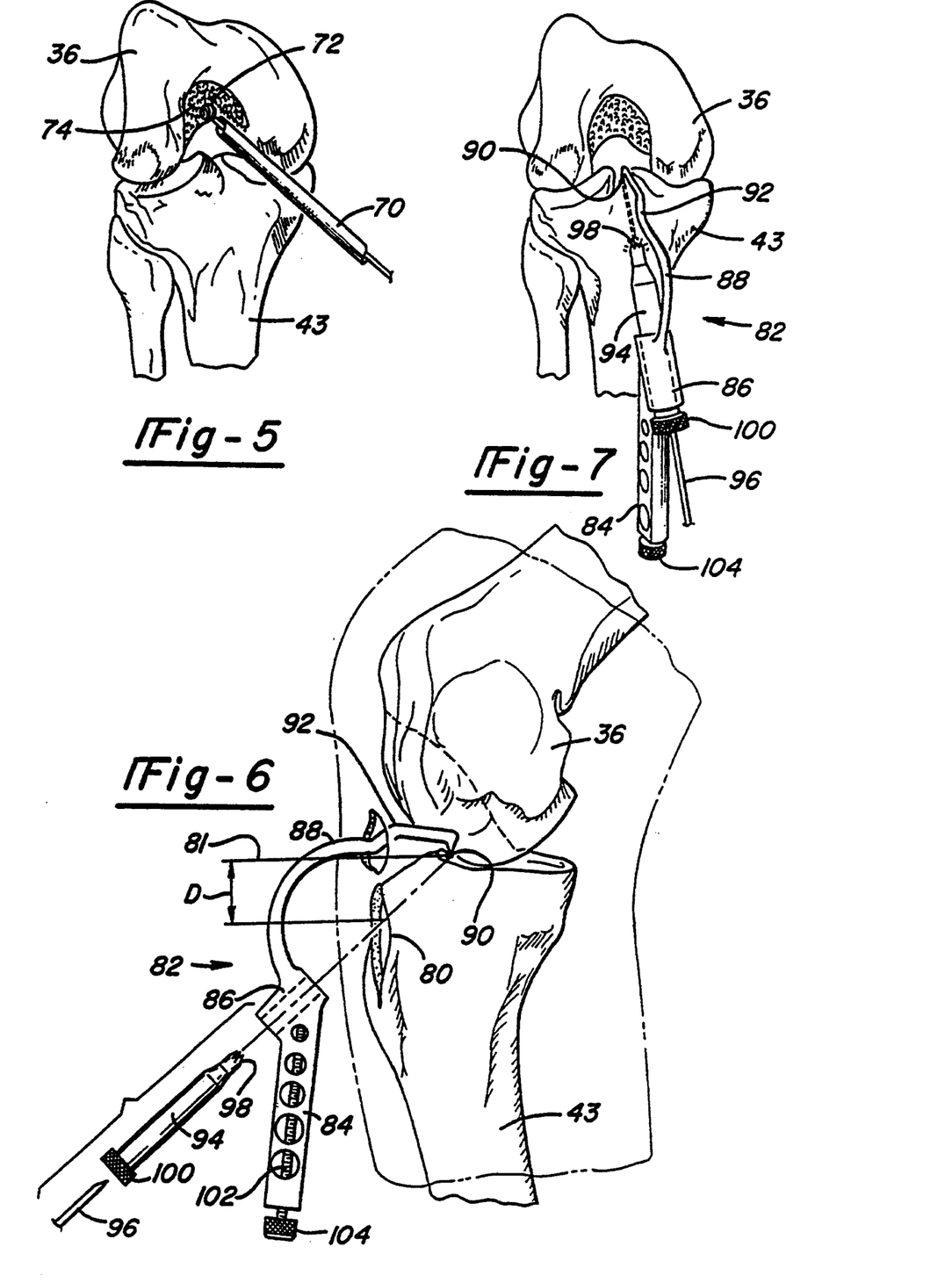
FIG. 5 is a schematic perspective view of the "notchplasty" procedural step for ACL reconstruction in accordance with the present invention.
FIGS. 6 and 7 illustrate an endoscopic tibia drill guide and its use in accordance with the present invention.

Selective lateral and superior expansion "notchplasty" of the intercondylar notch 74 is achieved using, initially, appropriate gouges and then, a motorized cutter and abrader 70. Part of this conventional procedure is shown in FIG. 5. During notchplasty, the 25° arthroscopic viewing is generally positioned from the anterolateral portal. The motorized cutter and abrader 70 are inserted through the anteromedial portal. The motorized cutter (not shown) is used to remove the soft tissue. The rotating abrader tip 72 is used to remove the bone in the intercondylar notch 74 in the femur 36. The notchplasty is performed to increase visibility to the proposed femoral attachment site and to avoid impingement of the ACL substitute during use after it is implanted. Again, care should be taken during this procedure to avoid damaging the PCL.

After the notchplasty, the tibial tunnel is formed. The placement of the portion of the osseous tunnel in the tibia, as well as the placement of the portion of the tunnel in the femur is important. The two tunnels should be formed so that they enter the joint at the proper anatomic attachment points. These points are preferably on the knee joint surfaces where the original ACL was attached.

Figure 8:
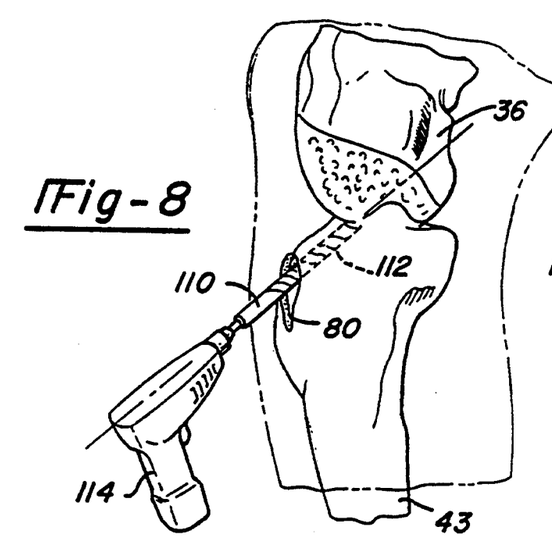
FIG. 8 illustrates the formation of the tibial tunnel using a cannulated drill bit over-drilling a K-wire pin.

The preferred manner of forming the tibial tunnel is shown in FIGS. 6-8. A vertical incision 80 (FIG. 6) is made medial to the infrapatellar tendon, and approximately 2 cm distal to the joint line 81. The periosteum is incised and elevated exposing the tibial cortex. A unique drill guide instrument 82 is used to select the proper tibial attachment and tunnel drilling sites. The guide 82 has a handle 84, a collar 86 and a roughly semicircular shaped tibia point selector member 88. The member 88 has an aimer point 90 at the angle near the tip and has a bent portion 92 to prevent contact with the femur and the patella. The aimer point 90 is positioned endoscopically on the appropriate tibial anatomic attachment site. The attachment site is identified by probing through the anteromedial portal with the aimer point 90. The point 90 is positioned against the bone and the guide 82 is then manually held firmly in position.

Once the aimer point 90 is positioned in place, a drill sleeve (or "bullet") 94 is placed through the collar 86. The drill sleeve is hollow, having a passageway for placement therethrough of a sharp pointed 3/32" K-wire pin 96. The front end 98 of the bullet 94 has a sharp tri-point and the rear end has a knob 100 for ease of grasping and manipulation. Due to the shape and structure of the instrument 82, the collar 86 is positioned optimally so that the bullet 94 will contact the tibia 43 at a distance "D" 20-25 mm below the joint line 81. Once the tri-point bullet 94 is positioned in place, it is then locked in place in that position in the collar 86 by a long threaded rod 102 which is operated by knob 104. The rod 102 is threaded through a threaded opening (not shown) in the collar 86 and makes contact with the bullet 94. When the rod is rotated by the knob 104, it forces the bullet 94 into firm non-slipping engagement with the inner wall of the collar 86 holding the two members firmly locked together.

Once the drill guide 82 and bullet 94 are firmly set in place, the K-wire 96 is passed through the bullet 94 and drilled into and substantially through the tibia using a conventional surgical motorized drill. The bullet 94 is then released from the collar 86 and removed from the guide 82 leaving the K-wire in place. The drill guide 82 is also removed. The K-wire pin is then advanced (by hitting it with a mallet or the like) to assure that its position in the tibial stump is appropriate, and also to assure that the direction of the pin is correct in the vicinity of the femoral anatomic attachment point. The position and direction are viewed arthroscopically.

A cannulated drill bit 110 is selected corresponding to the size of the graft and placed over the K-wire 96 (FIG. 8). An 8–11 mm cannulated drill bit is selected if a semitendinosus tendon is being used as the graft. The tibial tunnel 112 for the graft is then drilled through the tibia using a conventional surgical motorized drill 114 and using the K-wire 96 as a guide. Where possible, the stump fibers of the original ACL are preserved as a biological covering for the graft. The edges at the two ends of the tunnel are smoothed and beveled using conventional rasp-type chamfering instruments in order to prevent later abrasion and damage to the graft.

As shown, the use of the drill guide instrument 82 allows the surgeon to drill an anatomic tunnel 112 from a point just 2 to 2.5 cm distal to the joint line and which accurately and reproducibly enters the joint at the anatomic attachment site. The instrument 82 ensures highly accurate, reproducible guide wire placement, while enabling the surgeon to create femoral and tibial tunnels with a reduced divergence angle and close to a straight line. The drill guide, as with all of the surgical instruments preferred for use in the specified, operation, is made from a autoclavical metal material, preferably stainless steel. A preferred drill guide system is available from Acufex Microsurgical, Inc., entitled "Endoscopic Drill Guide System" (Part No. 013650).

Figure 9A:
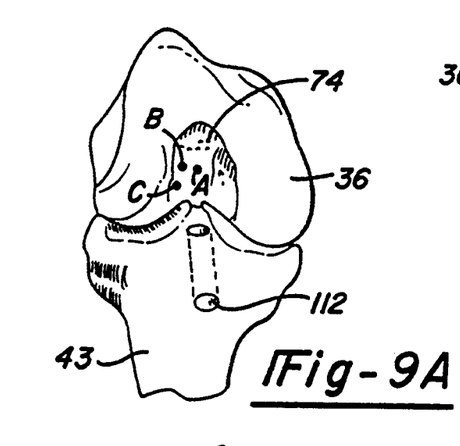
FIGS. 9A and 9B show various points for location of the femoral attachment site.
Figure 9B:
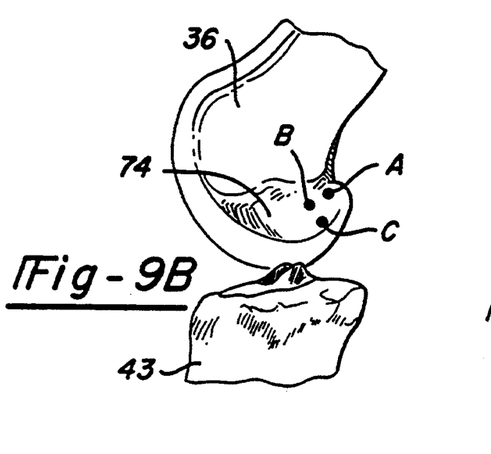

Once the tibial tunnel 112 is completed, the next step involves selecting the proper site in the femur 36 for the remainder of the osseous tunnel. As mentioned earlier, selection of the appropriate isometric point is important. As illustrated in FIGS. 9A and 9B, point A is proximal and high in the notch 74 and typically demonstrates an isometry pattern which mimics the normal ACL. Point B is distal (anterior as viewed arthroscopically) and generally demonstrates unacceptable elongation in flexion. Point C is lateral and posterior in the notch 74 and generally demonstrates excessive strain in extension.

Once the suggested femoral site is selected, it is tested isometrically to determine if it is the best possible site. This test procedure is shown in FIGS. 10A–16. A K-wire 96 is inserted through the tibial tunnel 112 and its point is used to make a small pilot hole 120 in the intercondylar notch 74 at the proposed femoral attachment site. Due to the size of the tunnel 112 compared with the size of the K-wire, it is possible to manipulate and move the K-wire in order to select the most appropriate point to make the hole 120.

Figure 10A:
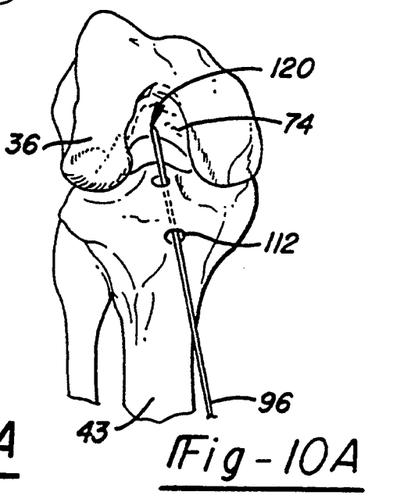
FIGS. 10A and 10B illustrate the marking and drilling of the proposed femoral attachment site and the configuration of a K-wire drill which can be used for this step in the procedure.
Figure 10B:
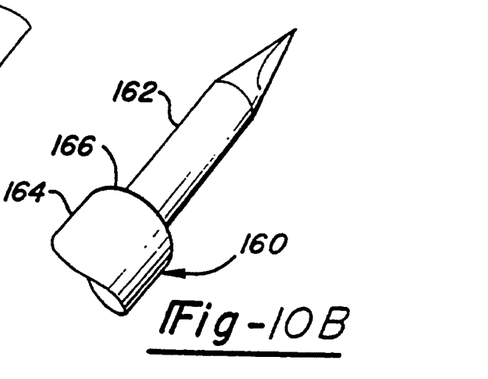
Figure 11:
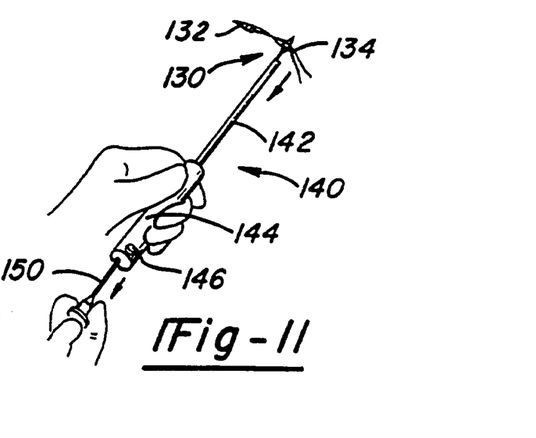
FIGS. 11–14 depict the anchor and driver system used as part of the procedure for isometrically determining the femoral attachment site for the graft.

Working with the knee flexed at a 90° angle, the pilot hole 120 at the proposed isometric site is drilled to an appropriate depth for attachment of an isometric anchor. A surgical motorized drill is used to advance the K-wire a preselected distance into the femur to allow easy attachment of the anchor. In order to assure that the K-wire is not advanced too far, a graduated K-wire (that is a K-wire with millimeter markings on it) or preferably a stepped K-wire (as shown in FIG. 10B) can be utilized. The stepped K-wire drill 160 has a reduced diameter end 162 separated from the main shaft 164 by a shoulder 166. Preferably, the diameter of the main shaft 164 is 0.118 inches, the diameter of the end 162 is 0.081 inches, and the length of the pilot K-wire from the shoulder 166 to the tip is 0.250 inches. The shoulder is used to prevent the K-wire from being advanced too far into the femur since it limits the depth of the drilled opening. For proper attachment of an anchor, the hole 120 in the femur should be drilled to a depth of approximately 6 mm.

Next, a small suture anchor is attached to the femur at the selected point in the drilled hole 120. The anchor 130 consists of a threaded peg 132 connected to No. 2 suture 134 through an eyelet 136 (see FIGS. 11–13). A unique hand held cannulated driver 140 is used to deliver the anchor 130 to the proposed site and fasten it in place. The driver is cannulated having an elongated hollow sleeve 142 and a hollow handle 144. The handle has a tie button or suture affixation post 146 on it. The suture 134 is threaded down through the driver 140 by use of a conventional suture retriever 150 (FIG. 11), preferably the Acufex Suture Retriever by Acufex Microsurgical, Inc. The suture 134 is used to pull the threaded anchor peg 132 tightly into the end 143 of the driver sleeve 142 and the suture is then secured tightly in place by wrapping it around the post 146.

Figures 12, 13, 14, 15A, 16:
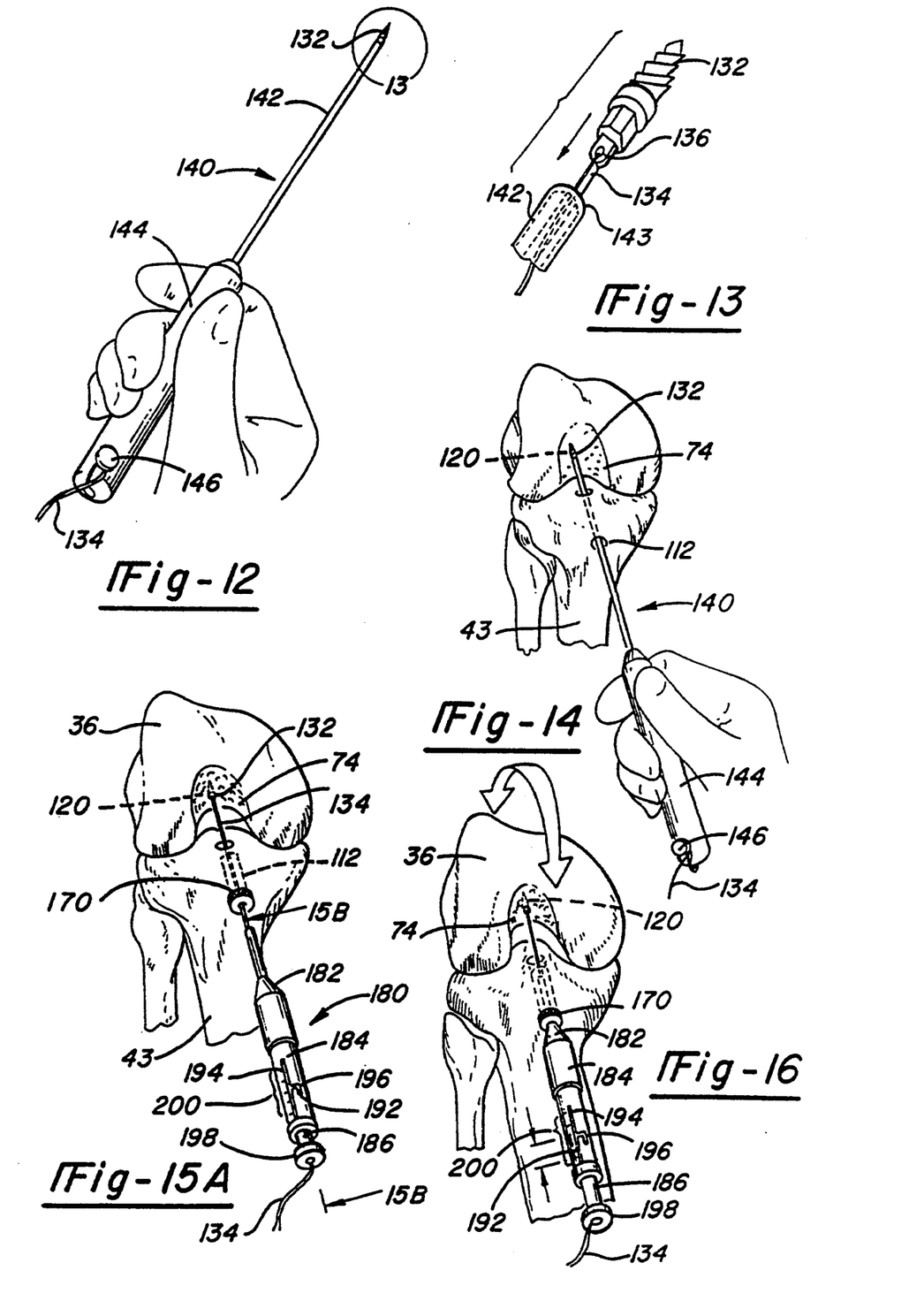
FIGS. 15A and 16 depict use of an isometer in isometrically determining the femoral attachment site.

As shown in FIG. 13, the rear end of the threaded peg 132 has a non-circular cross-section (preferably a hexagonal shape) and the open top end 143 of the sleeve 142 has a corresponding mating cross-sectional size and shape. In this manner, when the anchor 130 is seated firmly in place in the driver 140, rotation and manipulation of the driver 140 will have an identical corresponding effect on the anchor 130. The preferred anchors and drivers for use with the present invention are the "Isotac" anchors and "Isotac" drivers marketed by Acufex Microsurgical, Inc. The "Isotac" anchor (threaded peg) preferably has an outer diameter of 0.093 inches and fits tightly into the pilot hole.

After the driver 140 is loaded with the anchor 130 as shown in FIG. 12, the unit is passed through the tibial tunnel 112, as shown in FIG. 14, and the anchor peg 132 is set in place in the opening 120 drilled in the femur. The driver 140 is manually rotated which, in turn, screws the threaded peg 132 into the bone until it is securely fixed in place. Viewing arthroscopically, the anchor is rotated into the femur until the end 143 of the driver sleeve 142 abuts the femoral surface. After the anchor 130 is set in place, the driver 140 is removed and set aside, leaving the suture 134 extending through the tunnel.

The suture 134 is threaded through a centering plug 170 and the plug is then inserted into the tibial tunnel 112 (FIGS. 15A and 16). A suture passer or retriever can be used if desired to thread the suture through the guide. The suture 134 is also passed through a spring loaded strain gauge (or isometer) 180. (If desired, the suture can be passed through the guide 170 and isometer 180 in one step).

Figure 15B:
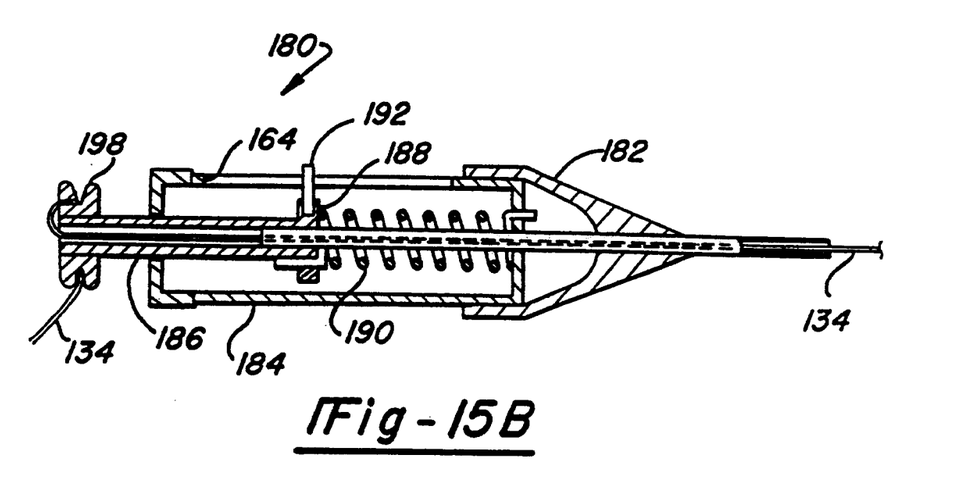
FIG. 15B is a cross-sectional view of the isometer shown in FIGS. 15A and 16.

The isometer 180 has a front end 182 which is adapted to abut and mate with the guide 170, a housing 184 and a plunger member 186, as best shown in FIG. 15B. The plunger 186 fits within the housing 184 in a sliding telescopic relationship. The internal end 188 of the plunger 186 is connected to a coil spring 190. The coil spring, in turn, is connected to the inside of the housing. The end 188 also has a locking post 192 which is adapted to slide along slot 194 or be locked in position in a bayonet or "J"-shaped slot 196. The spring 190 biases the member 186 relative to the housing. The plunger 186 also has a suture anchoring member 198 at its outer or external end.

A scale 200 in millimeters is arranged along the edge of the slot 194 so readings can be made of the position of the post 192 relative to it. Preferably, the center of the scale at the entrance to the J-shaped slot 196 is set at "zero" so that positive and negative strain gauge readings from the zero point can be read in millimeters depending on the movement of the post 192 during operation of the isometer 180.

With the isometer 180 locked to the zero position (i.e. with the post 192 positioned in the slot 196), the patient's knee is positioned at approximately 45° flexion. The front end 182 of the isometer is abutted against the guide 170 and the slack is taken up in the suture 134. The suture 134 is securely positioned and tightened around the member 198 at the end of the plunger 186. This is shown in FIG. 16.

To check on the isometry of the positioning of the proposed femoral attachment site, the isometer is unlocked and the knee is manually taken through the range of motion permitted by the operating site. As the knee is moved and the suture affected thereby, the plunger is translated relative to the housing in a proportional manner. The movement of the post along the slot provides a reading of the strain on the suture.

An optimal reading reveals a 0–1 mm change in length while flexing and a 2–3 mm elongation (tightening) in terminal extension. A 2–3 mm elongation pattern caused by interior rotation of the tibia is also preferred. If readings within these ranges are achieved, then the correct femoral attachment site has been determined and the hole 120 is at the appropriate position. In rare circumstances, such as a variation in surgical technique (i.e. tibia site selection), failure of secondary restraint, or interference by the PCL, the preferred readings may be affected. However, except for these rare circumstances, if the readings are not within these ranges, then another proposed site is selected and the isometric test repeated. This involves drilling another hole with a K-wire, attaching another suture anchor in the new hole with the cannulated driver, and repeating the testing process with the centering plug and isometer.

Once isometry is confirmed and the appropriate femoral site selected, the driver 140 is used to unscrew and remove the anchor peg 132. The anchor 130 is then discarded. The knee joint is returned to the 90° position and the sharp K-wire 96 is directed through the tibial tunnel 112 and into the hole 120 in the femur. The K-wire is then drilled into the femur sufficiently to hold it in place and act as the drill guide for forming the closed-end femoral tunnel.

Figures 17, 18:
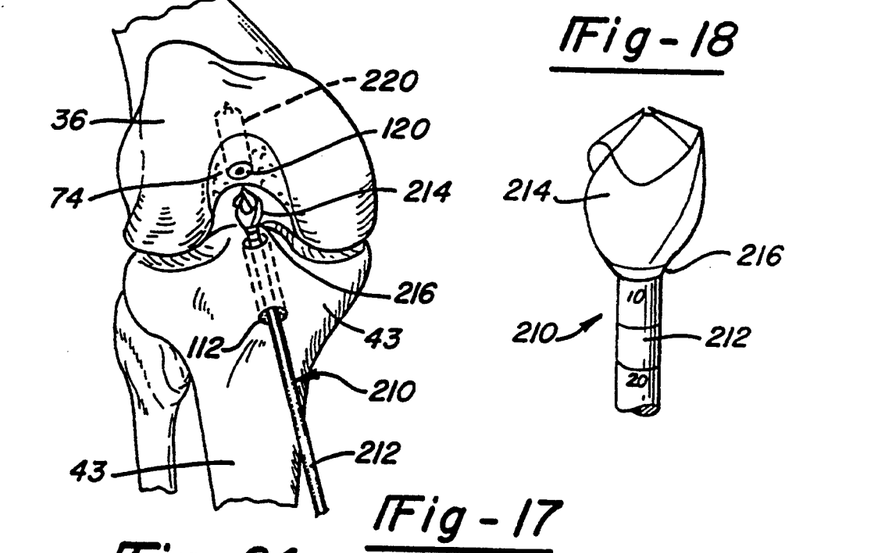
FIG. 17 illustrates the drilling of the closed-end femoral tunnel in accordance with the present invention.
FIG. 18 depicts the preferred drill bit or reamer used to form the femoral tunnel in accordance with the present invention.

The K-wire is over-drilled with a cannulated drill bit or reamer. This is shown in FIG. 17. The preferred drill bit or reamer 210, which is shown in FIGS. 17 and 18, has an abbreviated (shortened length of approximately 7 mm) drilling head 214, and a reduced sized shank 212 (5–6 mm) which is smaller in diameter than the drilling head 214. The shank is gradually sloped to the head 214 along annular surface 216 to make a smooth transition and prevent snagging or damage to soft tissue such as the PCL and tibial tunnel when the reamer 210 is manipulated in the knee joint and eventually removed from the tibial tunnel. The sloped surface 216 permits easy removal of the reamer from the knee joint. The reduced diameter shank 212 also importantly allows variation of placement of the femoral drilling site.

A closed end tunnel or socket 220, preferably about 2–2.5 cm in length, is drilled into the femur by the reamer 210 after the reamer has passed beyond the PCL. The depth of the tunnel is determined by noting calibrations on the reamer 210. A tunnel 2.5 cm in depth is sufficient for semitendinosus grafts. If a patellar tendon is being used for the graft, then the depth of the tunnel should be correlated to the length of the bone plug on the tendon.

Once the femoral tunnel is drilled, the edge of the tunnel which opens into the knee joint is smoothed and chamfered with a conventional rasp. This prevents abrasion and potential damage to the graft.

FIGS. 19, 20, 21 and 22 show the manner in which patellar tendon grafts are positioned and secured into the osseous tunnels in accordance with one embodiment of the invention. (A typical patellar tendon graft is shown and described above with reference to FIG. 4). The tendon 60 is harvested with bone plugs 62 and 64 at its ends.

Figure 19:
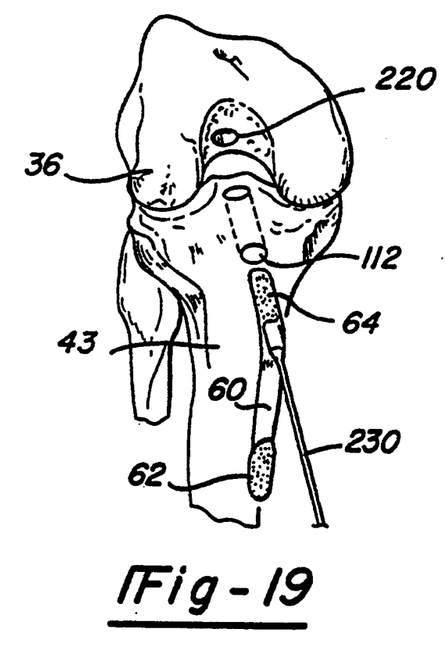
FIGS. 19, 20, 21 and 22 illustrate positioning and securing of patellar tendon grafts in accordance with one embodiment of the present invention.
Figure 20:
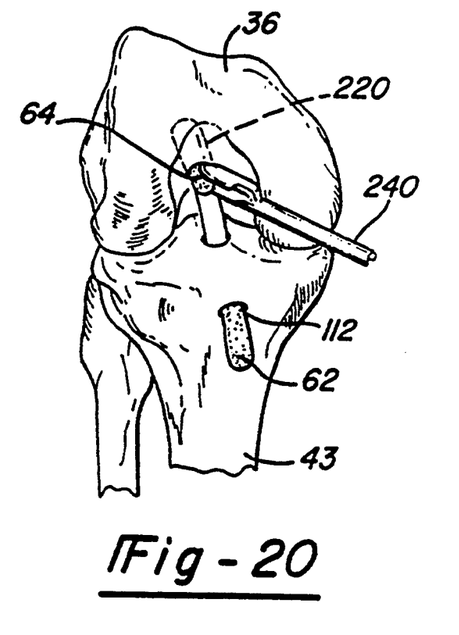

A plunger instrument 230 is used to introduce the leading bone plug 64 into the joint through the tibial tunnel 112 (FIG. 19). Once the bone plug 64 has passed through the tibial tunnel and into the knee joint, an arthroscopic bone grasper 240 introduced through the anteromedial portal is used to insert the bone plug into the closed-end femoral tunnel 220 (FIG. 20). Alternately, a passing pin can be advanced from the end of the femoral socket through to the lateral femoral cortex, piercing the quadriceps muscle and the subcutaneous and skin layers. The pin is used to pull sutures placed on the patellar bone block through the femoral socket and in turn pull the bone block into the socket.

Figure 21:
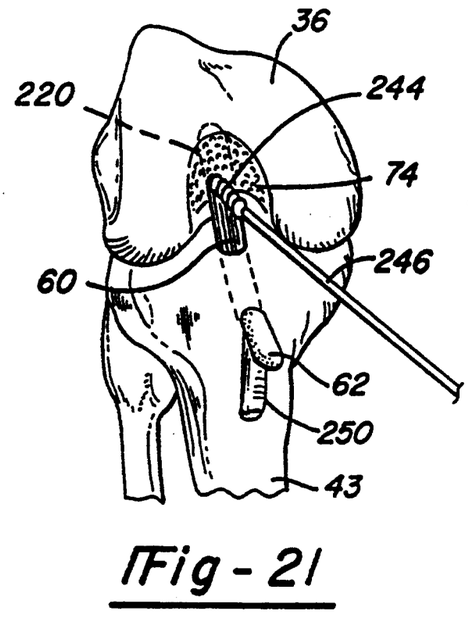
Figure 21A:
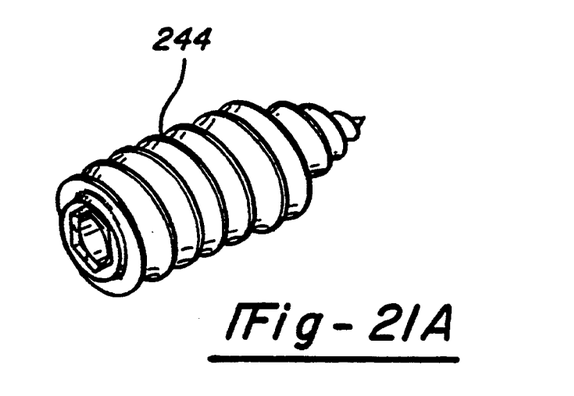
FIG. 21A illustrates an interference screw used to secure the patellar tendon graft in the femoral socket.
Figure 22:
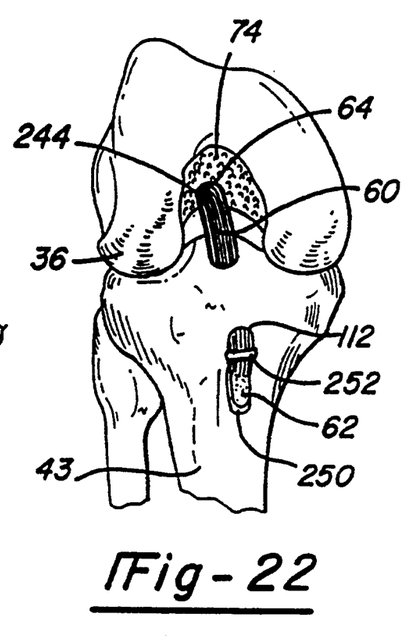

Proximal fixation of the patellar tendon graft in the femoral tunnel 220 is preferably obtained by use of a 5.5 mm endoscopic screw 244 (FIGS. 21 and 21A). The screw 244 is introduced into the knee joint through the anteromedial portal and affixed in place with an arthroscopic screw driver 246 or the like. The interference screw abuts against the bone plug 64 and holds it firmly in place in the femoral tunnel. In order to prevent damage to the tendon, care should be taken not to turn the screw 244 into or against the tendon graft 60 during insertion. The preferred endoscopic interference screw is made by Acufex Microsurgical, Inc. The screw is self-tapping, has a cork-screw shaped tip for self-engagement, and the rows of threads after the first two rows are machined or smoothed so they will not damage or cut the graft. This screw is shown in FIG. 21A.

A trough 250 is prepared in the tibia below the opening of the tibial tunnel 112 for placement of the distal bone plug 62. A surgical staple 252 is used to affix the bone plug 62 into the trough 250.

Once the graft is secured in place, it is viewed arthroscopically and probed to confirm that the correct tension has been achieved. The knee is also moved through its normal range of motion to assure that impingement of the graft does not occur.

The above technique for ACL reconstruction using a patellar tendon graft uses a blind-hole tunnel in the femur and eliminates the necessity for a lateral incision in the thigh or top of the femur for positioning or affixation of the graft. This significantly reduces the trauma and scarring to the patient and facilitates faster healing and rehabilitation.

Figures 23, 24, 25:
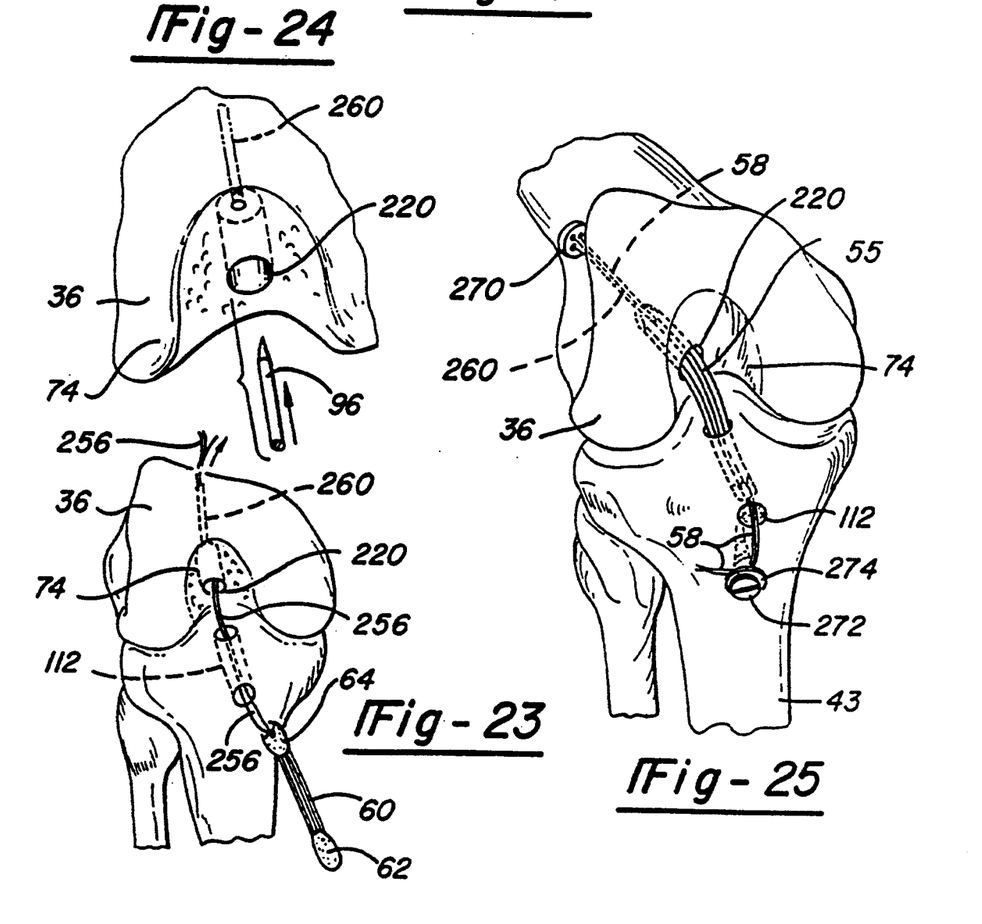
FIG. 23 illustrates an alternate method for securing a patellar tendon graft in place.
FIG. 24 illustrates one step in the procedure for securing semitendinosus grafts in accordance with another embodiment of the present invention.
FIG. 25 depicts the positioning and securing of semitendinosus grafts in accordance with the present invention.

Alternately, if another affixation technique is preferred for the proximal end of the patellar tendon graft in the femur which does not utilize a screw, it is possible in accordance with the present invention, to utilize only a small lateral incision above the femur and still avoid much of the trauma and scarring associated with previously known ACL repair and reconstruction methods. For this alternate method, the patellar tendon graft has No. 2 Ticron sutures 256 stitched onto the bone plug 64, as shown in FIG. 23. A passing channel 260 is also drilled (with a K-wire) past the closed end of the femoral tunnel 220 and through the lateral femur surface. A small lateral incision is made to expose the passing channel site in the lateral surface of the femur. A suture passing guide wire (not shown) is then positioned through the tibial and femoral tunnels and out through the passing channel opening and used to pull the graft through the osseous tunnels until the proximal bone plug 64 is seated firmly in the femoral tunnel. Passage of the graft is observed arthroscopically to confirm smooth advancement into the closed-end femoral tunnel. The sutures 256 are secured at the lateral femoral cortex over a fixation button in a conventional manner. Preferably, the button is a Delrin fixation button 2 mm in thickness, 14–17 mm in diameter and with chamferred suture openings to prevent damage to the sutures. Distal fixation of bone plug 62 is obtained by stapling the bone plug into a trough as described above, or in any conventional manner.

In order to position and secure semitendinosus tendon grafts in place with suture leaders (as shown in FIG. 3), a passing channel 260 is drilled past the closed-end of the femoral tunnel 220 with a K-wire drill 96 (FIG. 24). A small lateral incision is made and the lateral femoral cortex is exposed around the passing channel which extends through the femoral surface.

A suture passing guide (or pull through wire) is passed through the tibial and femoral tunnels and out through the lateral femoral cortex. The ends 58 of the No. 2 Ticron sutures which are attached to the composite graft 55 are drawn through the knee and femur 36 with the pull through wires, thereby pulling the semitendinosus graft segments 52 and 54 into position in the osseous tunnels. The passage of the bundled graft 55 is observed arthroscopically in order to make sure it advances smoothly into the closed-end femoral tunnel. A probe can be used to assist in the entry into the femoral tunnel.

The ends 58 of the sutures are secured at the lateral femoral cortex by use of a fixation button 270. Again, a strong 2 mm thick Delrin button with chamferred suture openings is preferred. Once the proximal end of the graft 55 has been seated in the femoral tunnel, the sutures are passed through openings in the button and tied off firmly in place. In order to secure the distal end of the semitendinosus graft, a fixation post (screw) 272 is attached to the tibia 1-2 cm below the entrance to the tibial tunnel 112. A hole is first drilled in the tibia at the point where the fixation post is to be positioned. The hole is drilled through the tibia ending in the strong bone layer on the opposite side of the tibia. The hole is tapped with screw threads and a small headed fixation screw is selected of the appropriate length.

After the fixation post 272 is screwed in most of the way (about 75–95%), the graft is pulled and tensioned distally through the osseous tunnels and the ends 58 of the distal sutures 56 are tied firmly around the post. The screw is then turned down tightly until it is set firmly in the tibia. A washer 274 either attached to or positioned immediately under the head of the fixation screw helps hold the tied sutures in place when the screw is tightened.

Similar to the procedure mentioned above with respect to implantation of patellar grafts, the secured semitendinosus tendon grafts are inspected and probed arthroscopically to confirm that the correct tension and positioning has been achieved. The patient's knee is also manually manipulated through its range of motion in order to assure that graft impingement does not occur. Any necessary decompression of the intercondylar notch is carefully performed if any points of impingement on the graft are observed.

Finally, the wounds around the knee are closed, the tourniquet is removed, and appropriate postoperative care is followed.

While the best modes for carrying out the invention have been described in detail, those familiar with the art to which this invention relates will recognize various alternatives, designs and embodiments for practicing the invention as defined by the following claims.

What is claimed:

1. A method of forming a passageway in a first bone at a joint, defined by the first bone and a second bone, in patient, the method comprising:
   forming a first passage through tissue into the joint to provide access to the first bone;
   providing a drill having an abbreviated, shortened length drilling head and a smooth, cylindrical shank of smaller diameter than the drilling head, the drilling head defining a distal surface inclined toward the distal tip of the drilling head and a proximal surface inclined toward the shank;
   selecting a drilling site on the first bone;
   passing the drilling head of the drill through the first passage; and
   placing the drilling head against the selected site beyond soft tissue within the joint, so that only the smooth shank is capable of contacting the soft tissue after drilling begins, to avoid snagging of the soft tissue by the drilling head, and forming a passageway into the first bone by drilling with the drilling head.

2. The method of claim 1 wherein the drill is cannulated for receiving a guide wire therethrough, and passing the drilling head includes guiding the drilling head over a guide wire having a tip resting within the first bone at the selected site.

3. The method of claim 1 wherein the proximal surface of the drilling head forms a smooth transition with the shank.

4. The method of claim 1 wherein forming the first passage into the joint includes drilling a tunnel through the second bone.

5. The method of claim 1 wherein forming the passageway establishes a closed end tunnel in the first bone.

6. A method of forming a passageway in a femur at a knee joint, defined by the femur and a tibia, in a patient, the method comprising:
   forming a first passage through tissue into the joint to provide access to the femur;
   providing a drill having an abbreviated, short-length drilling head and a smooth, uninterrupted cylindrical shank of smaller diameter than the drilling head, the drilling head defining a distal surface inclined toward the distal tip of the drilling head and a proximal surface inclined toward the shank and forming a smooth transition with the shank, and the drill being cannulated for receiving a guide wire therethrough;
   selecting a drilling site on the femur;
   inserting a guide wire into the first passage and into the femur at the selected site;

passing the drilling head of the drill over the guide wire and through the first passage; and placing the drilling head against the selected site beyond soft tissue within the joint, so that only the smooth shank is capable of contacting the soft tissue after drilling begins, to avoid snagging of the soft tissue by the drilling head, and forming a passageway into the femur by drilling with the drilling head.

7. The method of claim 6 wherein forming the first passage into the joint includes drilling a tunnel through the tibia.

8. The method of claim 7 wherein the drill further includes means for determining the depth of the drill into the passageway.

9. The method of claim 8 wherein the means for determining is a scale carried by the shaft.

10. The method of claim 9 wherein forming the passageway establishes a closed end tunnel in the femur.

* * * * *